United States Patent [19]

Kranz

[11] 4,162,280

[45] Jul. 24, 1979

[54] PREPARATION OF PHOSPHORYLATED AMIDINES

[75] Inventor: Eckart Kranz, Wuppertal, Fed. Rep. of Germany

[73] Assignee: Bayer Aktiengesellschaft, Leverkusen, Fed. Rep. of Germany

[21] Appl. No.: 887,899

[22] Filed: Mar. 17, 1978

[30] Foreign Application Priority Data

Apr. 9, 1977 [DE] Fed. Rep. of Germany ....... 2715933

[51] Int. Cl.² .............................................. C07F 9/24
[52] U.S. Cl. .............................. 260/968; 260/326.61; 544/157; 546/21
[58] Field of Search ............... 260/968, 944, 945, 959, 260/326.61; 544/157; 546/21

[56] References Cited

U.S. PATENT DOCUMENTS

| | | | |
|---|---|---|---|
| 2,965,667 | 12/1960 | Tolkmith | 260/968 |
| 3,801,679 | 4/1974 | Hoffman et al. | 260/945 |
| 3,888,951 | 6/1975 | Hoffman et al. | 260/945 |
| 4,000,268 | 12/1976 | Sirrenberg et al. | 260/945 X |

FOREIGN PATENT DOCUMENTS

2517101 4/1976 Fed. Rep. of Germany ........... 260/950

OTHER PUBLICATIONS

Chem. Ber. 101,1 (1968) pp. 41–50.

*Primary Examiner*—Anton H. Sutto
*Attorney, Agent, or Firm*—Sprung, Felfe, Horn, Lynch & Kramer

[57] ABSTRACT

Preparation of a phosphorylated amidine of the formula

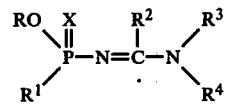

wherein X is oxygen or sulfur and R, $R^1$, $R^2$, $R^3$ and $R^4$ are various organic radicals, which comprises reacting a phosphoric acid ester-amide of the formula

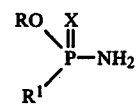

with a carboxamide of the formula

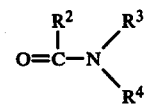

at a temperature between about 0° and 50° C., and then reacting the mixture with a base. Advantageously the reaction is effected at about 0° to 15° C. in the presence of an aliphatic or aromatic optionally chlorinated hydrocarbon or an alcohol as an inert solvent, and in the presence of a catalyst.

9 Claims, No Drawings

PREPARATION OF PHOSPHORYLATED AMIDINES

The present invention relates to an unobvious process for the preparation of certain phosphorylated amidines.

Phosphorylated amidines are known pesticides (see, for example, German Offenlegungsschriften (German Published Specifications) 2,261,230, 2,312,738 and 2,451,911). They may be obtained by reacting phosphoric acid ester-amides with amide-acetals, optionally in the presence of a solvent (see, for example, U.S. Pat. Nos. 3,888,951 and 4,000,268).

The industrial application of that process is associated with considerable difficulties with regard to the preparation of the amide-acetals, for example of dimethylformamide-dimethylacetal. Yields of only between 50–70% of theory are achieved, a high expenditure on distillation and of time being necessary in order to separate the acetal from the solvent. The process in practice is therefore uneconomic and of severely limited usefulness.

Furthermore, it is known that the above-mentioned amidines are obtained when phosphorylated iminoformic acid alkyl esters are reacted with amines, optionally in the presence of an organic solvent (see, for example, U.S. Pat. No. 3,888,951).

That process has the disadvantage that the required starting materials, that is to say the phosphorylated iminoformic acid alkyl esters, can only be obtained in yields of between 40 and 75% of theory. Moreover, the iminoformic acid esters can be purified by distillation only in very small amounts since the boiling point is too close to the decomposition point. Even when a thin-film evaporator is used, the phosphorylated iminoformic acid esters cannot be prepared safely on an industrial scale (see, for example, Chem. Ber. 101, 1 (1968) 41–50 and German Offenlegungsschrift (German Published Specification) 2,517,101). A further disadvantage of the process is that the ortho-esters required for the preparation are very expensive and in addition must be employed in excess.

There is therefore great interest in a process which can avoid these difficulties and which can give the desired products not only in good yields but also in high purity.

The present invention provides a process for the preparation of a phosphorylated amidine of the general formula

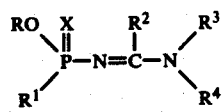

(I), in which
R represents alkyl or aryl,
$R^1$ represents alkyl, alkoxy, alkylthio, alkenylthio, aralkylthio, mono- or di-alkylamino, dialkenylamino, halogenoalkoxy or phenyl,
$R^2$ represents hydrogen, alkyl or aryl,
$R^3$ and $R^4$, which can be identical or different, each represent alkyl or alkenyl or
$R^3$ and $R^4$, with the nitrogen atom to which they are attached, form a heterocyclic ring which can optionally be interrupted by a further heteroatom and
X represents oxygen or sulphur, in which a phosphoric acid ester-amide of the general formula

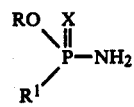

(II), in which
R, $R^1$ and X have the meanings stated above, is reacted with a carboxamide of the general formula

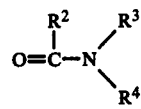

(III), in which
$R^2$, $R^3$ and $R^4$ have the meanings stated above, in the presence of a catalyst at a temperature between about 0° and 50° C., optionally in the presence of an organic solvent, and the reaction mixture is then reacted with a base.

Preferably, R represents straight-chain or branched alkyl with 1 to 8 carbon atoms or phenyl which can optionally carry one or more substituents selected independently from halogen (especially chlorine, bromine or fluorine), straight-chain or branched alkyl with 1 to 6 (especially 1 to 4) carbon atoms, carbalkoxy with 1 to 6 (especially 1 to 4) carbon atoms in the alkoxy radical, halogenoalkyl with 1 to 4 carbon atoms (especially trifluoromethyl), nitro, cyano and alkylthio with 1 to 6 (especially 1 to 4) carbon atoms, $R^1$ represents straight-chain or branched alkyl, alkoxy or alkylthio each with 1 to 8 carbon atoms, straight-chain or branched mono- or di-alkylamino with 1 to 6 (especially 1 to 3) carbon atoms per alkyl radical, straight-chain or branched dialkenylamino with up to 6 (especially with up to 4) carbon atoms per alkenyl radical, benzylthio, allylthio, propenylthio, butenylthio, straight-chain or branched halogenoalkoxy (especially chloroalkoxy) with 1 to 8 (especially 1 to 6) carbon atoms, or phenyl, $R^2$ represents hydrogen or straight-chain or branched alkyl with 1 to 6 (especially 1 to 3) carbon atoms or, less preferably, phenyl, and $R^3$ and $R^4$ are identical and each represent straight-chain or branched alkyl with 1 to 8 (especially 1 to 3) carbon atoms or straight-chain or branched alkenyl with up to 6 (especially with 3 or 4) carbon atoms or $R^3$ and $R^4$, together with the nitrogen atom to which they are bonded, represent a morpholino, piperidino or pyrrolidino ring.

It is surprising that the process according to the invention can proceed in a smooth and uniform manner under these reaction conditions and give, in high purity and very good yields, the desired end products having the formula (I), which could hitherto be prepared on an industrial scale by the methods indicated above only with the difficulties mentioned.

Compared with the known methods for the preparation of phosphorylated amidines, the process according to the present invention has a number of advantages. Thus, only readily available starting materials are required, which can be reacted in an easily controllable process and with high yields to give the desired products. The amidines obtainable according to the process can be prepared in high purity since the impurities formed can be removed by simple operations. The impurities can usually be removed by washing out with water, or they are highly volatile and can be removed by distillation, for example in a thin-film evaporator. Furthermore, it is highly advantageous that, under the reaction conditions indicated, the process can be carried out as a "one-pot reaction," which increases the efficiency of the process. Moreover the wide applicability of the process for obtaining any desired phosphorylated amidine within a large class is to be singled out; it is not restricted to the preparation of particular representatives of this class of compounds, such as, for example, the O,O-dialkylphosphoryl-amidines.

If, for example, O S-dimethylthionothiophosphoric acid diester-amide, dimethylformamide and dimethyl sulphate are used as starting materials, the course of the reaction according to the process can be represented by the following equation:

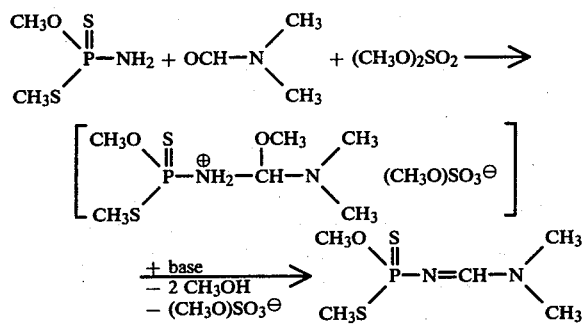

The phosphoric acid ester-amides (II) to be used as starting materials are already known (see, for example, published Dutch Patent Specification 6,911,925 and German Offenlegungsschrift (German Published Specification) 2,135,349 and U.S. Pat. No. 3,911,058).

Examples of these which may be mentioned are: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-ethyl-O-n-propyl-, O-ethyl-O-iso-propyl-, O-ethyl-O-n-butyl-, O-ethyl-O-sec.-butyl-, O-n-propyl-O-n-butyl-, O-n-propyl-O.sec.-butyl-, O-n-propyl-O-iso-butyl-, O-iso-propyl-O-n-butyl-, O-methyl-O-phenyl-, O-methyl-O-(2-chloro-phenyl)-, O-methyl-O-(2,4-dichloro-phenyl)-, O-methyl-O-(2,4,6-trichloro-phenyl)-, O-methyl-O-(2-nitro-phenyl)-, O-methyl-O-(4-nitro-phenyl)-, O-methyl-O-(2-cyano-phenyl)-, O-methyl-O-(4-cyano-phenyl)-, O-methyl-O-(4-trifluoromethyl-phenyl)-, O-methyl-O-(2-methyl-4-trifluoromethyl-phenyl)-, O-methyl-O-(4-methylthio-phenyl), O-methyl-O-(4-ethylthiophenyl)-, O-methyl-O-(2-methoxy-phenyl)-, O-methyl-O-(2-ethoxy-phenyl)-, O-methyl-O-(4-methoxy-phenyl)-, O-methyl-O-(4-ethoxy-phenyl)-, O-methyl-O-(4-n-propoxyphenyl)-, O-methyl-O-(2-carbomethoxy-phenyl)-, O-methyl-O-(2-carbethoxy-phenyl)-, O-methyl-O-(2-carbo-n-propoxy-phenyl)-, O-methyl-O-(4-carbomethoxy-phenyl)-, O-methyl-O-(4-carbethoxy-phenyl)-, O-methyl-O-(4-carbo-n-propoxyphenyl)-, O-ethyl-O-phenyl-, O-ethyl-O-(2-chloro-phenyl)-, O-ethyl-O-(2,4-dichloro-phenyl)-, O-ethyl-O-(2,4,6-trichloro-phenyl)-, O-ethyl-O-(2-nitro-phenyl)-, 0-ethyl-O-(4-nitro-phenyl)-, O-ethyl-O-(2cyano-phenyl)-, O-ethyl-O-(4-cyano-phenyl)-, O-ethyl-O-(4-trifluoromethyl-phenyl)-, O-ethyl-O-(2-methyl-4-trifluoromethyl-phenyl)-, O-ethyl-O-(4-methylthio-phenyl)-, O-ethyl-O-(4-ethylthio-phenyl)-, O-ethyl-O-(2-methoxy-phenyl), O-ethyl-O-(2-ethoxy-phenyl)-, O-ethyl-O-(4-methoxy-phenyl)-, O-ethyl-O-(4-ethoxy-phenyl)-, O-ethyl-O-(4-n-propoxy-phenyl)-, O-ethyl-O-(2-carbomethoxy-phenyl)-, O-ethyl-O-(2-carbethoxy-phenyl)-, O-ethyl-O-(2-carbo-n-propoxy-phenyl)-, O-ethyl-O-(4-carbomethoxy-phenyl)-, O-ethyl-O-(4-carbethoxy-phenyl)-, O-ethyl-O-(4-carbo-n-propoxy-phenyl)-, O-n-propyl-O-phenyl-, O-n-propyl-O-(2-chloro-phenyl)-, O-n-propyl-O-(2,4-dichloro-phenyl)-, O-n-propyl-O-(2,4,6-trichloro-phenyl)-, O-n-propyl-O-(2-nitro-phenyl)-, O-n-propyl-O-(4-nitro-phenyl)-, O-n-propyl-O-(2-cyano-phenyl)-, O-n-propyl-O-(4-cyano-phenyl)-, O-n-propyl-O-(4-trifluoromethyl-phenyl)-, O-n-propyl-O-(2-methyl-4-trifluoromethyl-phenyl)-, O-n-propyl-O-(4-methylthio-phenyl)-, O-n-propyl-O-(4-ethylthio-phenyl)-, O-n-propyl-O-(2-methoxy-phenyl)-, O-n-propyl-O-(2-ethoxy-phenyl)-, O-n-propyl-O-(4-methoxy-phenyl)-, O-n-propyl-O-(4-ethoxy-phenyl)-, O-n-propyl-O-(4-n-propoxy-phenyl)-, O-n-propyl-O-(2-carbomethoxy-phenyl)-, O-n-propyl-O-(2-carbethoxy-phenyl)-, O-n-propyl-O-(2-carbo-n-propoxy-phenyl)-, O-n-propyl-O-(4-carbo-methoxy-phenyl)-, O-n-propyl-O-(4-carbethoxy-phenyl)-, O-iso-propyl-O-phenyl)-, O-iso-propyl-O-(2-chloro-phenyl)-, O-iso-propyl-O-(2,4-dichloro-phenyl)-, O-iso-propyl-O-(2,4,6-trichloro-phenyl)-, O-iso-propyl-O-(2-nitro-phenyl)-, O-iso-propyl-O-(4-nitro-phenyl)-, O-iso-propyl-O-(2-cyano-phenyl)-, O-iso-propyl-O-(4-cyano-phenyl)-, O-iso-propyl-O-(4-trifluoromethyl-phenyl)-, O-iso-propyl-O-(4-methylthio-phenyl)-, O-iso-propyl-O-(4-ethylthio-phenyl)-, O-iso-propyl-O-(2-methoxy-phenyl)-, O-iso-propyl-O-(2-ethoxy-phenyl)-, O-iso-propyl-O-(2-methyl-4-trifluoromethyl-phenyl)-, O-iso-propyl-O-(4-methoxy-phenyl)-, O-iso-propyl-O-(4-ethoxy-phenyl)-, O-iso-propyl-O-(4-n-propoxy-phenyl)-, O-iso-propyl-O-(2-carbomethoxy-phenyl)-, O-iso-propyl-O-(2-carbethoxy-phenyl)-, O-iso-propyl-O-(2-carbo-n-propoxy-phenyl)-, O-iso-propyl-O-(4-carbomethoxy-phenyl)-, O-iso-propyl-O-(4-carbethoxy-phenyl)- and O-iso-propyl-O-(4-carbo-n-propoxy-phenyl)-phosphoric acid di-ester-amide and the corresponding thiono analogues, furthermore O,S-dimethyl-, O-methyl-S-ethyl-, O-methyl-S-n-propyl-, O-methyl-S-iso-propyl-, O-methyl-S-n-butyl-, O-methyl-S-sec.-butyl-, O-methyl-S-iso-butyl-, O-ethyl-S-methyl-, O,S-diethyl-, O-ethyl-S-n-propyl-, O-ethyl-S-iso-propyl-, O-ethyl-S-n-butyl-, O-ethyl-S-iso-butyl-, O-ethyl-S-sec.-butyl-, O-n-propyl-S-methyl-, O-n-propyl-S-ethyl-, O-n-propyl-S-iso-propyl-, O-n-propyl-S-n-butyl-, O-n-propyl-S-iso-butyl-, O-n-propyl-S-sec.-butyl-, O-iso-propyl-S-methyl-, O-iso-propyl-S-ethyl-, O-iso-propyl-S-n-propyl-, O-iso-propyl-S-n-butyl-, O-iso-propyl-S-iso-butyl- and O-iso-propyl-S-sec.-butyl-thiolphosphoric acid diester amides and the corresponding thiono analogues, and in addition O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl-, O-sec.-butyl-N-iso-propyl-, O-methyl-N,N-dimethyl-, O-methyl-N,N-diethyl-, O-methyl-N,N-di-n-propyl-, O-methyl-N,N-di-iso-propyl-, O-ethyl-N,N-dimethyl-, O-ethyl-N,N-diethyl-, O-ethyl-N,N-di-n-propyl-, O-ethyl-N,N-di-iso-propyl-, O-n-propyl-N,N-dimethyl-, O-n-propyl-N,N-diethyl-, O-n-propyl-N,N-di-n-propyl-, O-n-propyl-N,N-di-iso-propyl-, O-iso-propyl-N,N-dimethyl-, O-iso-propyl-N,N-diethyl-, O-iso-propyl-N,N-di-n-propyl-, O-iso-propyl-N,N-di-iso-propyl-, O-n-butyl-N,N-dimethyl-, O-n-butyl-N,N-diethyl-, O-n-butyl-N,N-di-n-propyl-, O-n-butyl-N,N-di-iso-propyl-, O-tert.-butyl-N,N-dimethyl-, O-tert.-butyl-N,N-di-ethyl-, O-tert.-butyl-N,N-di-n-propyl-, O-tert.-butyl-N,N-di-iso-propyl-, O-iso-butyl-N,N-dimethyl-, O-iso-butyl-N,N-diethyl-, O-sec.-butyl-N,N-dimethyl- and O-sec.-butyl-N,N-diethyl-phosphoric acid ester-diamide and the corresponding thiono analogues.

The carboxamides (III) which are also to be used as starting materials are likewise known (see, for example, Houben-Weyl "Methoden der organischen Chemie" ("Methods of Organic Chemistry") Volume 11/2, page 27 et seq.). Examples of these which may be mentioned are: N,N-dimethyl-, N,N-diethyl-, N,N-di-n-propyl-, N,N-di-iso-propyl-, N,N-di-n-butyl-, N,N-di-sec.-butyl-, N,N-di-iso-butyl- and N,N-diallyl-formamide and the corresponding acetamides, N-formyl-morpholine, N-formylpiperidine and N-formylpyrrolidine.

The process according to the invention can be carried out without or with the use of a suitable solvent or diluent. Possible solvents or diluents are virtually all the inert organic solvents, especially aliphatic or aromatic, optionally chlorinated hydrocarbons, such as benzene, toluene, xylene, chlorobenzene and o-dichlorobenzene, and alcohols, such as methanol, ethanol, propanol and isopropanol.

Examples which may be mentioned of the catalysts to be used are: dimethyl or diethyl sulphate, thionyl chloride, phosgene, phosphorus oxytrichloride or oxytribromide, phosphorus pentachloride, zinc chloride and acetic anhydride, as well as the catalysts which are used in formylation reactions, such as, for example, aldehyde syntheses by Vilsmeier's method (see H. Kranch and W. Kunz, Reaktionen der Organischen Chemie (Reactions of Organic Chemistry), Hütig-Verlag, Heidelberg, 1976, pages 392-394).

All the customary acid-binding agents can be used as bases. Alkali metal carbonates, alcoholates or hydroxides, such as sodium carbonate, potassium carbonate, sodium methylate, sodium ethylate, potassium methylate, potassium ethylate, sodium hydroxide or potassium hydroxide, as well as aliphatic, aromatic or heterocyclic amines, for example tertiary amines such as triethylamine, trimethylamine, dimethylaniline, dimethylbenzylamine and pyridine, have proved particularly suitable.

The reaction temperature can be varied within a relatively wide range. In general, the reaction is carried out between about 0° and 50° C., preferably about 0 to 30° C. and especially about 0° to 15° C.

In general, the reaction is allowed to proceed under normal pressure.

For carrying out the process according to the invention, the catalyst, optionally in a suitable diluent, is usually initially introduced and the carboxamide is added dropwise at room temperature. After stirring the mixture for one or more hours, the phosphoric acid ester-amide derivative, in most cases dissolved in an organic solvent, is added. After further stirring the mixture for one or more hours, the base is added and the reaction mixture is then worked up in the customary manner by distilling off the solvent, cooling the residue, adding water and extracting the aqueous phase with an organic solvent. The organic phase is worked up by drying and distilling off the solvent.

In most cases, the process products are colorless to pale yellow- colored liquids, which in most cases can be identified and characterized by their refractive index or by gas chromatography. If the compounds are obtained in the crystalline form, they are characterized by their melting points.

The phosphorylated amidines which can be prepared according to the present process are highly active pesticidal active compounds (see, for example, German Offenlegungsschriften (German Published Specifications) 2,312,738 and 2,517,101; and U.S. Pat. Nos. 3,940,457, 3,949,022, 3,975,523 and 4,000,268).

The compounds according to the present invention can be used, for example, for combating insect and acarid pests, amongst which are included the following:
from the order of the Tysanura, for example *Lepisma saccharina;*
from the order of the Collembola, for example *Onychiurus armatus;*
from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;*
from the order of the Dermaptera, for example *Forficula auricularia;*
from the order of the Isoptera, for example Reticulitermes spp.;
from the order of the Anoplura, for example *Phylloxera vastatrix,* Pemphigus spp., *Pediculus humanus corporis,* Haematopinus spp. and Linognathus spp.;
from the order of the Mallophaga, for example Trichodectes spp. and Damalinea spp.;
from the order of the Thysanoptera, for example *Hercinothrips femoralis* and *Trips tabaci;*
from the order of the Heteroptera, for example Eurygaster spp., *Dysdercus intermedius, Piesma quadrata, Cimex lectularius, Rhodnius prolixus* and Triatoma spp.;
from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Emposaca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;
from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubi-* lalis, *Ephestia keuhniella, Galleria mellonella, Cacoecia podana, Capua reticulana, Choristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*;

from the order of the Siphonaptera, for example *Xenopsylla cheopis* and Ceratophyllus spp.; and from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The examples which follow illustrate the process according to the invention in more detail.

EXAMPLE 1

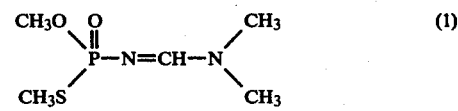

126 g (1.0 mol) of dimethyl sulphate were initially introduced into a 2 liter three necked flask. 73 g (1.0 mol) of dimethylformamide were added dropwise at room temperature in the course of about 30 minutes and the mixture was subsequently stirred for 16 hours. 155 g (0.81 mol) of O,S-dimethylthiolphosphoric acid diester-amide (73.4% pure), dissolved in 150 ml of methanol, were subsequently added dropwise, to the adduct thus prepared, at room temperature in the course of 30 minutes. The mixture was stirred for a further 3 hours and a solution of 54 g (1.0 mol) of sodium methylate in 350 ml of methanol was then added dropwise in the course of one hour at room temperature. The methanol was subsequently distilled off up to a bath temperature of 120° C. The mixture was allowed to cool and 500 ml of water were added. The aqueous phase was then extracted three times (300 ml, 150 ml, 150 ml) with chloroform. The combined organic phases were dried over sodium sulphate and the solvent was distilled off. Finally, the residue was freed from highly volatile impurities in a thin-film evaporator (130° C./0.1–0.3 mm Hg). The sump product was filtered through kieselgur. The crude yield was 96.4%; after incipient distillation: 83.1%; filtered through Kieselgur: 78.5%. The content according to gas chromatography was 96.9%.

EXAMPLE 2

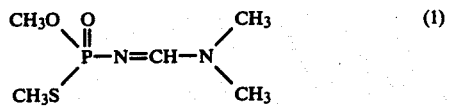

(1)

143 g (1.2 mol) of thionyl chloride were added dropwise to 87.6 g (1.2 mol) of dimethylformamide at 20°–25° C. in the course of one hour. The mixture was subsequently stirred for one hour at room temperature and 196 g (1.0 mol) of 72% pure O,S-dimethylthiolphosphoric acid diester-amide in 200 ml of methylene chloride were added dropwise at 0°–5° C. in the course of about 45 minutes. The mixture was stirred for a further 1 hour at 0° to 10° C. and 200 ml of water were added dropwise at the same temperature. 426.6 g (4.8 mol) of 45% strength sodium hydroxide solution were subsequently added dropwise at 0° to 10° C. in the course of about 20 minutes. The mixture was then filtered, the residue on the filter was washed with methylene chloride and the phases of the filtrate were separated by washing the aqueous phase once with 100 ml of methylene chloride and distilling off the solvents from the organic phases. The yield was 201.7 g (102.8% of theory).

EXAMPLE 3

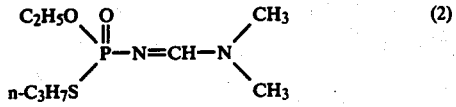

(2)

143 g (1.2 mol) of thionyl chloride were added dropwise to 87.6 g (1.2 mol) of dimethylformamide at 20°–25° C. The mixture was subsequently stirred for one hour at room temperature. 199.3 g (1 mol) of O-ethyl-S-n-propyl-thionophosphoric acid diester-amide (91.8% pure) in 200 ml of toluene were added dropwise at a temperature of 0°–10° C. The mixture was stirred for a further 4 hours at the same temperature, then 200 ml of water and subsequently 426.6 g (4.8 mol) of 45% strength sodium hydroxide solution were added dropwise at 0°–10° C.; the mixture was filtered and the residue was washed once with toluene. The phases of the filtrate were separated; the aqueous phase was extracted once with 200 ml of toluene and the combined organic phases were evaporated. The yield was 230 g (96.6% of theory) and the product was 94.3% pure according to the gas chromatogram.

It will be appreciated that the instant specification and examples are set forth by way of illustration and not limitation, and that various modifications and changes may be made without departing from the spirit and scope of the present invention.

What we claim is:

1. A process for the preparation of a phosphorylated amidine of the formula

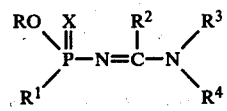

in which
R is alkyl or aryl,
$R^1$ is alkyl, alkoxy, alkylthio, alkenylthio, aralkylthio, mono- or di-alkylamino, dialkenylamino, halogenoalkoxy or phenyl,
$R^2$ is hydrogen, alkyl or aryl,
$R^3$ and $R^4$ each independently is alkyl or alkenyl or
$R^3$ and $R^4$, with the nitrogen atom to which they are attached, form a heterocyclic ring which can optionally be interrupted by a further hetero-atom, and
X is oxygen or sulphur,
which comprises reacting a phosphoric acid ester-amide of the formula

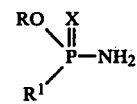

with a carboxamide of the formula

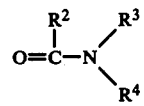

at a temperature between about 0° and 50° C. in the presence of a member selected from the group consisting of dimethyl sulphate, diethyl sulphate, thionyl chloride, phosgene, phosphorus oxytrichloride, phosphorus oxytribromide, phosphorus pentachloride, zinc chloride, acetic anhydride and a formylation Vilsmeier's aldehyde synthesis catalyst, and then reacting the mixture with a base.

2. A process according to claim 1, in which
R is alkyl with 1 to 8 carbon atoms, phenyl, or phenyl carrying at least one substituent selected from halogen, alkyl with 1 to 6 carbon atoms, carbaloxy with 1 to 6 carbon atoms in the alkoxy radical, halogenoalkyl with 1 to 4 carbon atoms, nitro, cyano or alkylthio with 1 to 6 carbon atoms,
$R^1$ is alkyl, alkoxy or alkylthio each with 1 to 8 carbon atoms, mono- or di-alkylamino with 1 to 6 carbon atoms per alkyl radical, dialkenylamino with up to 6 carbon atoms per alkenyl radical, benzylthio, allylthio, propenylthio, butenylthio, halogenoalkoxy with 1 to 8 carbon atoms, or phenyl, $R^2$ is hydrogen or alkyl with 1 to 6 carbon atoms, and $R^3$ and $R^4$ are identical and each is alkyl with 1 to 8 carbon atoms or alkenyl with up to 6 carbon atoms, or $R^3$ and $R^4$, together with the nitrogen atom to which they are bonded, form a morpholino, piperidino or pyrrolidino ring.

3. A process according to claim 1, in which the reaction is effected in the presence of an inert organic solvent.

4. A process according to claim 3, in which the solvent is an aliphatic or aromatic, optionally chlorinated hydrocarbon or is an alcohol.

5. A process according to claim 1, in which the base is an alkali metal carbonate, an alkali metal alcoholate, an alkali metal hydroxide or an aliphatic, aromatic or heterocyclic amine.

6. A process according to claim 1, in which the reaction is effected at about 0° to 30° C.

7. A process according to claim 2, in which the reaction is effected at about 0° to 15° C. in the presence of an aliphatic or aromatic optionally chlorinated hydrocarbon or an alcohol as an inert solvent, and the base is an alkali metal carbonate, an alkali metal alcoholate, an alkali metal hydroxide or an aliphatic, aromatic or heterocyclic amine.

8. A process according to claim 1, in which the reaction is effected in the presence of a member selected from the group consisting of thionyl chloride, phosgene, phosphorus oxytrichloride, phosphorus oxytribromide, phosphorus pentachloride, zinc chloride, acetic anhydride and a formylation Vilsmeier's aldehyde synthesis catalyst.

9. A process according to claim 1, wherein the base is an alkali metal carbonate or hydroxide.

* * * * *